(12) United States Patent
Smith et al.

(10) Patent No.: US 9,273,074 B2
(45) Date of Patent: Mar. 1, 2016

(54) FORMYLPYRROLE-BASED HETEROCYCLES FOR NUCLEIC ACID ATTACHMENT TO SUPPORTS

(71) Applicant: Illumina, Inc., San Diego, CA (US)

(72) Inventors: Ryan Christopher Smith, San Diego, CA (US); Randall Smith, San Diego, CA (US); Xiaodong Zhao, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 14/512,181

(22) Filed: Oct. 10, 2014

(65) Prior Publication Data

US 2015/0031833 A1 Jan. 29, 2015

Related U.S. Application Data

(63) Continuation of application No. 13/009,797, filed on Jan. 19, 2011, now Pat. No. 8,883,764.

(51) Int. Cl.
| | |
|---|---|
| *C07F 9/6503* | (2006.01) |
| *C07F 9/6506* | (2006.01) |
| *A61K 31/675* | (2006.01) |
| *C07F 9/572* | (2006.01) |
| *C07H 21/00* | (2006.01) |

(52) U.S. Cl.
CPC ............ *C07F 9/5728* (2013.01); *A61K 31/675* (2013.01); *C07F 9/6506* (2013.01); *C07F 9/65031* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 6,548,652 | B2 | 4/2003 | Lukhtanov et al. |
| 7,592,435 | B2 | 9/2009 | Milton et al. |
| 7,785,796 | B2 | 8/2010 | Balasubramanian et al. |
| 7,795,424 | B2 | 9/2010 | Liu et al. |

OTHER PUBLICATIONS

Green et al., J. Med. Chem., 1969, 12, 326-329.
James et al., Organic Syntheses, 1959, vol. 39, 30 [Coll. vol. 4, 539 (1963)].
Kearney et al., Angew. Chem. Int. Ed., 2006, 45, 7803-7806.
Nielsen et al., Nucleic Acids Research, 1986, 14(18), 7391-7403.
Soderquist et al., J. Org. Chem., 1981, 46, 4599-4600.
Wiederholt et al., Nucleic Acids Research, 1999, 27(12), 2487-2493.
Xie et al., Org. Process Res. Dev., 2005, 9(6), 730-737.
Zahran et al., J. Chem. Sci., 2009, 121(4), 455-462.

*Primary Examiner* — Michael Barker
(74) *Attorney, Agent, or Firm* — Jones Day

(57) ABSTRACT

A compound has Formula I:

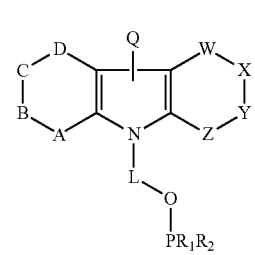

A, B, C, D, W, X, Y, and Z are independently selected from hydrogen, optionally substituted $C_1$-$C_6$ alkyl, optionally substituted $C_1$-$C_6$ alkoxy, aryl, aldehyde, protected aldehyde, CH, N, O, S, null, and bond; Q is selected from aldehyde, protected aldehyde, and null, at least one of A, B, C, D, W, X, Y, Z, or Q is an aldehyde or protected aldehyde; the bonds between each of A-B, B-C, C-D, W-X, X-Y, and Y-Z are selected from single bond, double bond, triple bond, and no bond; L is a linker selected from a $C_1$-$C_{12}$ alkyl, aralkyl, and aryl, any of which is optionally substituted; one or more methylene unit ($CH_2$) of the $C_1$-$C_{12}$ alkyl is optionally replaced by any combination of oxygen, carbonyl(C=O), and NH; and $R_1$ and $R_2$ are independently selected from —$NR_3R_4$, halogen, $C_1$-$C_8$ alkoxy, aralkoxy, alkenyloxy, alkynyloxy, and $OCH_2CH_2CN$; $R_3$ and $R_4$ are independently a $C_1$-$C_4$, straight chain or branched alkyl group.

26 Claims, No Drawings

FORMYLPYRROLE-BASED HETEROCYCLES FOR NUCLEIC ACID ATTACHMENT TO SUPPORTS

This application is a continuation application of U.S. patent application Ser. No. 13/009,797, filed Jan. 19, 2011, which is incorporated herein by reference in its entirety.

The present invention relates generally to reagents for solid phase chemistry, and more specifically to reagents useful for immobilizing substrates on a support.

BACKGROUND OF THE INVENTION

Numerous methods are available for the attachment of substrates to solid supports. Despite the array of methods that can be employed, there is still a need to develop immobilization chemistry for applications such as high throughput nucleic acid analysis where efficiency of coupling and high loading density are desirable. The present invention provides reagents and methods to meet this need and provides related advantages as well.

SUMMARY OF THE INVENTION

In some aspects, embodiments disclosed herein relate to a compound of Formula I:

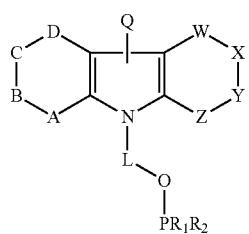

I wherein A, B, C, D, W, X, Y, and Z are independently selected from the group consisting of hydrogen, optionally substituted $C_1$-$C_6$ alkyl, optionally substituted $C_1$-$C_6$ alkoxy, aryl, aldehyde, protected aldehyde, CH, N, O, S, null, and bond; Q is selected from the group consisting of aldehyde, protected aldehyde, and null, with the proviso that at least one of A, B, C, D, W, X, Y, Z, or Q is an aldehyde or protected aldehyde; the bonds between each of A-B, B-C, C-D, W-X, X-Y, and Y-Z are selected from the group consisting of single bond, double bond, triple bond, and no bond; L is a linker selected from a $C_1$-$C_{12}$ alkyl, aralkyl, and aryl, any of which is optionally substituted; wherein one or more methylene unit ($CH_2$) of the $C_1$-$C_{12}$ alkyl is optionally replaced by any combination of oxygen, carbonyl(C=O), and NH; and $R_1$ and $R_2$ are independently selected from the group consisting of —$NR_3R_4$, halogen, $C_1$-$C_8$ alkoxy, aralkoxy, alkenyloxy, alkynyloxy, and $OCH_2CH_2CN$; wherein $R_3$ and $R_4$ are independently a $C_1$-$C_4$, straight chain or branched alkyl group.

Compounds of Formula I can be reacted with a nucleic acid via phosphorus-based chemistry to prepare nucleic acid conjugates of Formula II. Thus, in some aspects, embodiments disclosed herein relate to a compound of Formula II:

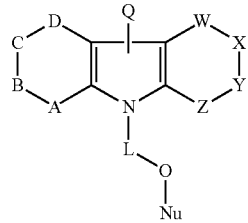

II wherein A, B, C, D, W, X, Y, and Z are independently selected from the group consisting of hydrogen, optionally substituted $C_1$-$C_6$ alkyl, optionally substituted $C_1$-$C_6$ alkoxy, aryl, aldehyde, protected aldehyde, CH, N, O, S, null, and bond; Q is selected from the group consisting of aldehyde, protected aldehyde, and null, with the proviso that at least one of A, B, C, D, W, X, Y, Z, or Q is an aldehyde or protected aldehyde; the bonds between each of A-B, B-C, C-D, W-X, X-Y, and Y-Z are selected from the group consisting of single bond, double bond, triple bond, and no bond; L is a linker selected from a $C_1$-$C_{12}$ alkyl, aralkyl, and aryl, any of which is optionally substituted; wherein one or more methylene unit ($CH_2$) of the $C_1$-$C_{12}$ alkyl is optionally replaced by any combination of oxygen, carbonyl(C=O), and NH; and Nu is a nucleic acid.

In some aspects, embodiments disclosed herein relate to modified nucleic acids of Formula II which possess an aldehyde or masked aldehyde that serves as a functional group handle to attach the nucleic acid to a support. The support is provided with an amino or masked amino group to facilitate immobilization of the aldehyde-modified nucleic acids of the invention via Schiff base chemistry. In some such embodiments, the resultant attached nucleic acid can be substantially irreversibly attached to the support by means of reduction of the Schiff base.

DETAILED DESCRIPTION OF THE INVENTION

The present invention is directed, in part, to reagents useful for the conjugation of a substrate, including nucleic acid substrates, to a solid support. Such reagents are exemplified by the pyrrole-containing compounds of Formula I. Pyrrole-containing heterocycles, such as pyrroles, indoles, isoindoles, carbazoles, pyrrolopyridines, pyrrolopyrazines, pyrrolopyrimidines, and pyrrolopyridizines and other nitrogen containing heterocycles containing active NH moieties, such as imidazoles, purines, and the like, are particularly suited for conjugation chemistry due to the flexible nature of the NH group for modular installation of linker and substrate.

Installation of a linking group (L) off the pyrrole NH group can be achieved via alkylation or acylation chemistry, for example, which is compatible with a wide array of structural linking group types. The flexibility of nitrogen alkylation and acylation chemistry allows any linking group type to be employed. In some embodiments, where the substrate is a nucleic acid, the linking group can terminate in an alcohol functional group or protected alcohol group. Once revealed, the alcohol can be functionalized to compounds of Formula I allowing entry into the phosphorus chemistry manifold for nucleic acid coupling, as shown in the general synthetic scheme below.

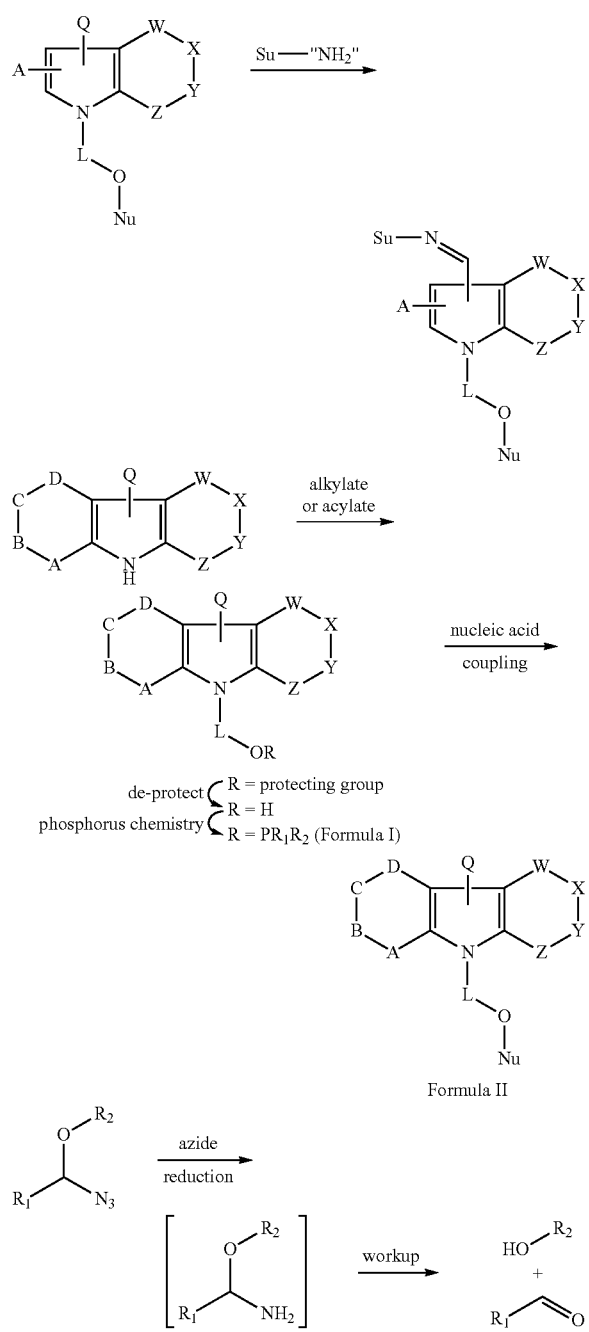

Through the ready ability to diversify the linking group, Applicants have found a useful subset of linker lengths that allow for high density attachment of nucleic acid to supports, although any linker length generally provides operable attachment to a support. In some such embodiments, a linker having a linear length ranging from between about 3 carbons to about 8 carbons is particularly useful. Moreover, the orthogonal nature of the Schiff base attachment chemistry used for immobilization and the linker chemistry, allows for flexibility in the order of attachment of nucleic acid (or other substrate), linker, and support. For example, the Schiff base attachment of the pyrrole-containing heterocycle, with or without the linker, can precede nucleic acid attachment. Similarly, the linker can be attached to the nucleic acid before the linker is attached to the pyrrole-containing heterocycle. In this latter scenario, the pyrrole-containing heterocycle can be immobilized for the conjugation step, or the heterocyclic core can be added in solution phase, and thereafter attached to the support.

Pyrrole-containing compounds of Formulas I and II also contain at least one aldehyde or masked aldehyde group. The aldehyde or aldehyde precursor provides the means for attachment to the support via Schiff base chemistry. Schiff base chemistry allows flexibility in providing reversibly bound nucleic acids or, if desired, the Schiff base imine (or iminium ion) can be reduced, providing a nominally irreversible attachment of the nucleic acid to the support. One skilled in the art will recognize that this "irreversible" attachment is not absolute and that other chemistries can be employed to remove such covalently bound nucleic acids.

The compounds of Formula I utilize phosphorus-based chemistry for the attachment of nucleic acids via 3'- or 5'-O-linkage along a phosphate backbone, however, one skilled in the art will recognize the flexibility of the heterocyclic core that allows entry to other bonding motifs, such as attachment via a nucleic acid base. For example, alkynyl substituted nucleobases can be used in conjunction with azide functionalized linkers, for example, to perform click chemistry. Moreover, while embodiments disclosed herein relate to the attachment of nucleic acids, in particular, to a support, the skilled artisan will recognize the applicability of minor variants of the disclosed synthetic schemes to immobilize any substrate, including, without limitation, small molecules, peptides, proteins, carbohydrates, and the like.

As used herein, the term "nucleic acid" is intended to mean at least two nucleotides covalently linked together. Nucleic acid encompasses the term oligonucleotide, polynucleotide, and their grammatical equivalents. A nucleic acid of the present invention will generally contain phosphodiester bonds, although in some cases nucleic acid analogs can have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and U.S. Pat. No. 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone can be done to facilitate the addition of labels, or to increase the stability and half-life of such molecules in physiological environments.

A nucleic acid of the present invention will generally contain a specific sequence of four nucleotide bases: adenine (A); cytosine (C); guanine (G); and thymine (T). Uracil (U) can also be present, for example, as a natural replacement for thymine when the nucleic acid is RNA. Uracil can also be used in DNA. A nucleic acid used in the invention can also include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. Exemplary non-native bases that can be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid of the invention can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil.

As used herein the term "array of nucleic acids" means a solid support having a plurality of spatially distinguishable nucleic acids disposed thereon or therein. The nucleic acids can be disposed in an ordered or random pattern of features. An individual feature can be, for example, a spatially isolated nucleic acid molecule, or an ensemble of nucleic acid molecules such as a cluster. An array can be a composite array comprising a plurality of individual arrays configured to allow processing of multiple samples. The individual arrays, referred to herein as "sub-arrays," include groups of nucleic acid features. Sub-arrays appear in distinct regions with in a larger array. The sub-arrays themselves can be ordered or non-ordered. Such sub-arrays can be optionally spatially addressable. Sub-arrays can include clusters of identical nucleic acids. An example of a composite array composed of individual sub-arrays is a microtiter plate having wells in which the plate as a whole is an array of nucleic acids (or composite array) while each individual well represents a sub-array within the larger composite array.

As used herein the term "support" refers to a substrate for immobilizing nucleic acids. A "support" is a material having a rigid or semi-rigid surface to which a nucleic acid array can be attached or upon which nucleic acids can be synthesized and/or modified. Supports can include any resin, microbead, glass, controlled pore glass (CPG), fused silica, polymer support, membrane, paper, plastic, plastic tube or tablet, plastic bead, glass bead, slide, ceramic, silicon chip, multi-well plate, nylon membrane, fiber optic, and PVDF membrane.

A support can include any flat wafer-like substrates and flat substrates having wells, such as a microtiter plate, including 96-well plates. Exemplary flat substrates include chips, slides, etched substrates, microtiter plates, and flow cell reactors, including multi-lane flow cell reactors having multiple microfluidic channels, such as the eight channel flow cell used in the cBot sequencing workstation (Illumina, Inc., San Diego, Calif.).

A support can also include beads, including magnetic beads, hollow beads, and solid beads. Beads can be used in conjunction with flat supports, such flat supports optionally also containing wells. Beads, or alternatively microspheres, refer generally to a small body made of a rigid or semi-rigid material. The body can have a shape characterized, for example, as a sphere, oval, microsphere, or other recognized particle shape whether having regular or irregular dimensions. The sizes of beads, in particular, include, without limitation, about 1 µm, about 2 µm, about 3 µm, about 5 µm, about 10 µm, about 20 µm, about 30 µm, about 40 µm, about 60 µm, about 100 µm, about 150 µm or about 200 µm in diameter. Other particles can be used in ways similar to those described herein for beads and microspheres.

The composition of a support can vary, depending for example, on the format, chemistry and/or method of attachment and/or on the method of nucleic acid synthesis. Support materials that can be used in accordance with the present disclosure include, but are not limited to, polypropylene, polyethylene, polybutylene, polyurethanes, nylon, metals, and other suitable materials. Exemplary compositions include supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "Microsphere Detection Guide" from Bangs Laboratories, Fishers Ind., which is incorporated herein by reference. A support particle can be made of cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, or TEFLON®. "Microsphere Detection Guide" from Bangs Laboratories, Fishers, Inc., hereby incorporated by reference in its entirety, is a helpful guide. Further exemplary supports within the scope of the present disclosure include, for example, those described in US Application Publication No. 02/0102578 and U.S. Pat. No. 6,429,027, both of which are incorporated herein by reference in their entirety.

The term "alkoxy," as used herein, alone or in combination, refers to an alkyl ether group, wherein the term alkyl is as defined below. Examples of suitable alkyl ether groups include methoxy, ethoxy, n-propoxy, iso-propoxy, n-butoxy, iso-butoxy, sec-butoxy, tert-butoxy, and the like.

The term "alkyl," as used herein, alone or in combination, refers to a straight-chain or branched-chain alkyl group containing from 1 to 20 carbon atoms. In certain embodiments, the alkyl group will comprise from 1 to 12 carbon atoms. In further embodiments, the alkyl group will comprise from 1 to 6 carbon atoms, which can optionally be used interchangeably with the term "lower alkyl" group. In yet further embodiments, the alkyl group will comprise from 1 to 4 carbon atoms, which can also be used interchangeably with the term "lower alkyl" group. Alkyl groups can be optionally substituted as defined herein. Examples of alkyl groups include methyl, ethyl, n-propyl, iso-propyl, n-butyl, iso-butyl, sec-butyl, tert-butyl, pentyl, iso-amyl, hexyl, heptyl, octyl, nonyl, decyl, undecyl, dodecyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" can include "alkylene" groups.

The term "aryl," as used herein, alone or in combination, means a carbocyclic aromatic system containing one, two or three rings wherein such polycyclic ring systems are fused together. The term "aryl" include, without limitation, aromatic groups such as phenyl, naphthyl, anthracenyl, and phenanthryl.

The term "aralkyl" or "arylalkyl," as used herein, alone or in combination, refers to an aryl group, as defined herein, attached to the parent molecular moiety through an alkyl group, as defined herein. An exemplary aralkyl is the benzyl group. Other aralkyl groups include, without limitation, phenylethyl, phenylpropyl, phenylbutyl, naphthylmethyl, naphthylethyl, napthylpropyl, anthracenylmethyl, anthracenylethyl, phenanthrylmethyl, and phenanthrylethyl.

The term "aralkoxy" or "arylalkoxy," as used herein, alone or in combination, refers to an aryl group, as defined herein, attached to the parent molecular moiety through an alkoxy group, as defined herein.

The term "alkene" or radical fragment "alkenyl," as used herein, alone or in combination, refers to a straight-chain or branched-chain hydrocarbon group having one or more double bonds and containing from 2 to 20 carbon atoms. In some embodiments, an alkene will comprise from 2 to 6 carbon atoms. The term "alkenylene" refers to a carbon-carbon double bond system attached at two or more positions such as ethenylene [(—CH═CH—), (—C::C—)]. Examples of suitable alkenyl groups include ethenyl, propenyl, 2-methylpropenyl, 1,4-butadienyl and the like. The term "alkenyl" can include "alkenylene" groups.

The term "alkenyloxy," as used herein, alone or in combination, refers to an alkenyl ether group, wherein the term alkenyl is defined herein. Examples of suitable alkenyl ether groups include allyloxy (2-propenoxy), vinyloxy (ethenoxy), 1-propenoxy, n-butenoxy, and the like.

The term "alkyne" or radical fragment "alkynyl," as used herein, alone or in combination, refers to a straight-chain or branched chain hydrocarbon group having one or more triple bonds and containing from 2 to 20 carbon atoms. In certain embodiments, the alkynyl group comprises from 2 to 6 carbon atoms. In further embodiments, the alkynyl group comprises from 2 to 4 carbon atoms. The term "alkynylene" refers to a carbon-carbon triple bond attached at two positions such as ethynylene (—C:::C—, —C≡C—). Examples of alkynyl groups include ethynyl, propynyl, hydroxypropynyl, butyn-1-yl, butyn-2-yl, pentyn-1-yl, 3-methylbutyn-1-yl, hexyn-2-yl, and the like. The term "alkynyl" can include "alkynylene" groups.

The term "alkynyloxy," as used herein, alone or in combination, refers to an alkynyl ether group, wherein the term alkynyl is as defined herein. Examples of suitable alkynyl ether groups include, ethynyloxy, 1-propynyloxy, propargyloxy (2-propynyloxy), butynyloxy, and the like.

The term "hydroxyalkyl," as used herein, alone or in combination, refer to an alkyl group, as defined herein, bearing a hydroxy moiety (—OH) on at least one carbon atom of the alkyl chain.

The term "halo," or "halogen," as used herein, alone or in combination, refers to fluorine, chlorine, bromine, or iodine.

The term "bond," as used herein, alone or in combination, refers to a covalent bond between two atoms and can include single, double, and triple bonds.

The term "null," as used herein means that the group is absent.

The term "protected," "masked," and "synthon," any of which can be used interchangeably, as defined herein, alone or in combination, refers to a synthetic precursor to the moiety to which it refers. For example, a protected aldehyde, refers to any synthetic precursor which can be reacted to unveil or acts as a synthetic equivalent to an aldehyde group. Protected aldehydes can include O,O-acetals, N,O-acetals, S,O-acetals, N,N-acetals, and N,S-acetals, cyanohydrins, and alkylated cyanohydrins. Other masked aldehydes, aldehyde synthons, or other synthetic equivalent to an aldehyde can include alkenes, which can be reacted via ozonolysis, dihydroxylation-periodate cleavage, or, the like. A synthon of an aldehyde need not have the same oxidation state as an aldehyde. For example an alcohol can be oxidized to an aldehyde or an ester or carboxylic acid can be reduced to an aldehyde. Suitable protecting groups for any organic functional group and the processes for their introduction and removal are known in the art (Theodora W. Greene and Peter G. M. Wuts, Protective Groups in Organic Synthesis, 3rd Edition, John Wiley & Sons, Inc., New York, 1999).

The term "optionally substituted" means the anteceding group can be substituted or unsubstituted. When substituted, the substituents of an "optionally substituted" group can include any of the substituents defined herein including, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents can be joined together to form a fused five-, six-, or seven-membered carbocyclic or heterocyclic ring consisting of zero to three heteroatoms, for example forming methylenedioxy or ethylenedioxy. An optionally substituted group can be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety can be defined as needed; in these cases, the optional substitution will be as defined, often immediately following the phrase, "optionally substituted with." The following substituent definitions are provided, which are within the scope of substituents embraced by the term optionally substituted, in addition to those substituents already defined above.

As used herein the term "lower alkyl ester" refers to a $C_1$-$C_6$ alkyl chain ester of a carboxylic acid. In some embodiments, a "lower alkyl ester" refers to a $C_1$-$C_4$ alkyl chain ester of a carboxylic acid. Representative esters include methyl, ethyl, propyl, butyl, pentyl, and hexyl esters. Any of the forgoing esters can be optionally branched. Such branched esters include iso-propyl esters, sec-butyl esters, iso-butyl esters and tert-butyl esters, for example.

The term "alkylamino," as used herein, alone or in combination, refers to an alkyl group attached to the parent molecular moiety through an amino group. Suitable alkylamino groups can be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) group wherein the term alkyl is as defined above and wherein the sulfur can be singly or doubly oxidized. Examples of suitable alkyl thioether groups include methylthio, ethylthio, n-propylthio, iso-propylthio, n-butylthio, iso-butylthio, sec-butylthio, tert-butylthio, methanesulfonyl, ethanesulfinyl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR2 group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which can themselves be optionally substituted. Additionally, R and R' can combine to form heterocycloalkyl, either of which can be optionally substituted.

The term "arylalkenyl" or "aralkenyl," as used herein, alone or in combination, refers to an aryl group attached to the parent molecular moiety through an alkenyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl group derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent group C6H4= derived from benzene. Examples include, but are not limited to, benzothiophene and benzimidazole.

The term "carbamate," as used herein, alone or in combination, refers to an ester of carbamic acid (—NHCOO—) which can be attached to the parent molecular moiety from either the nitrogen or acid end, and which can be optionally substituted as defined herein.

The term "O-carbamyl" as used herein, alone or in combination, refers to a —OC(O)NRR' group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which can optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "haloalkoxy," as used herein, alone or in combination, refers to a haloalkyl group attached to the parent molecular moiety through an oxygen atom.

The term "haloalkyl," as used herein, alone or in combination, refers to an alkyl group having the meaning as defined above wherein one or more hydrogens are replaced with a halogen. Specifically embraced are monohaloalkyl, dihaloalkyl and polyhaloalkyl groups. A monohaloalkyl group, for one example, can have an iodo, bromo, chloro or fluoro atom within the group. Dihalo and polyhaloalkyl groups can have two or more of the same halo atoms or a combination of different halo groups. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon group, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms can optionally be oxidized and the nitrogen heteroatom can optionally be quaternized. The heteroatom(s) O, N and S can be placed at any interior position of the heteroalkyl group. Up to two heteroatoms can be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom can be independently selected from the group consisting of nitrogen, oxygen, and sulfur. In certain embodiments, the heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl can comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups can be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imine" or "imino," as used herein, alone or in combination, refers to RN=.

The term "iminohydroxy," as used herein, alone or in combination, refers to N(OH)C— and N—O—.

The term "isocyanato" refers to a —NCO group.

The term "isothiocyanato" refers to a —NCS group.

The term "lower," as used herein, alone or in a combination, where not otherwise specifically defined, means containing from 1 to 6 carbon atoms, inclusive. In some embodiments, lower means containing from 1 to 4 carbon atoms, inclusive.

The term "lower aryl," as used herein, alone or in combination, means phenyl or naphthyl, which can be optionally substituted as provided.

The term "lower heteroalkyl," as used herein, alone or in combination, refers to a stable straight or branched chain, or cyclic hydrocarbon group, or combinations thereof, fully saturated or containing from 1 to 3 degrees of unsaturation, consisting of one to six atoms in which one to three can be heteroatoms selected from the group consisting of O, N, and S, and the remaining atoms are carbon. The nitrogen and sulfur atoms can optionally be oxidized and the nitrogen heteroatom can optionally be quaternized. The heteroatom(s) O, N and S can be placed at any interior or terminal position of the heteroalkyl group. Up to two heteroatoms can be consecutive, such as, for example, —CH$_2$—NH—OCH$_3$.

The term "lower heteroaryl," as used herein, alone or in combination, means either 1) monocyclic heteroaryl comprising five or six ring members, of which between one and four of the members can be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls can be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four can be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls can be unsaturated.

The term "lower amino," as used herein, alone or in combination, refers to —NRR', wherein R and R' are independently selected from the group consisting of hydrogen, lower alkyl, and lower heteroalkyl, any of which can be optionally substituted. Additionally, the R and W of a lower amino group can combine to form a five- or six-membered heterocycloalkyl, either of which can be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO3H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)2-.

The term "N-sulfonamido" refers to a RS(=O)$_2$NR'— group with R and R' as defined herein.

The term "S-sulfonamido" refers to a —S(=O)2NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR' group, with R and R' as defined herein.

The term "O-thiocarbamyl" refers to a —OC(S)NRR' group with R and R' as defined herein.

The term "thiocyanato" refers to a —CNS group.

Any definition herein can be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

In some embodiments, the present invention provides a compound of Formula III:

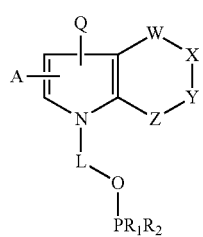

III wherein, W, X, Y, and Z are independently selected from the group consisting of CH, N, O, S, null, and bond; A is selected from the group consisting of aryl, hydrogen, hydroxyl, hydroxyalkyl, a C$_1$-C$_4$ straight chain or branched alkyl and alkoxy; P is phosphorus; Q is an aldehyde or protected aldehyde; wherein the bonds between each of W-X, X-Y, and Y-Z are selected from the group consisting of single bond, double bond, a triple bond, and no bond when W, X, Y, or Z is a bond; L is a linker selected from a C$_1$-C$_{12}$ alkyl, aralkyl, and aryl, any of which is optionally substituted; wherein one or more methylene unit (CH$_2$) unit of the C$_1$-C$_{12}$ alkyl is optionally replaced by any combination of oxygen, carbonyl(C=O), and NH; and R$_1$ and R$_2$ are independently selected from the group consisting of —NR$_3$R$_4$, halogen, C$_1$-C$_8$ alkoxy, aralkoxy, alkenyloxy, alkynyloxy, and OCH$_2$CH$_2$CN; wherein R$_3$ and R$_4$ are independently a C$_1$-C$_4$, straight chain or branched alkyl group.

In some embodiments, the pyrrole-containing compounds of Formulas III can be based on readily commercially available aldehyde heterocycles. Such heterocycles include, without limitation, pyrrole-2-carboxaldehyde, indole-3-carboxaldehyde, indole-2-carboxaldehyde, 5-methoxyindole-3-carboxaldehyde, 2-methylindole-3-carboxaldehyde, 5-benzyloxyindole-3-carboxaldehyde, 4-benzyloxyindole-3-carboxaldehyde, 5-fluoroindole-3-carboxaldehyde, 6-fluoroindole-3-carboxaldehyde, 5-methylindole-3-carboxaldehyde, 5-bromoindole-3-carboxaldehyde, 6-bromoindole-3-carboxaldehyde, 5-chloroindole-3-carboxaldehyde, 6-methylindole-3-carboxaldehyde, 7-methylindole-3-carboxaldehyde, 1-benzylindole-3-carboxaldehyde, 4-formyl-3,5-dimethyl-1H-pyrrole-2-carboxylic acid ethyl ester, 3,5-dimethylpyrrole-2-carboxaldehyde, 2-(4-chlorophenyl) indole-3-carboxaldehyde, 2-(4-fluorophenyl) indole-3-carboxaldehyde, 2-phenylindole-3-carboxaldehyde, 2,5-dimethylpyrrole-3-carboxaldehyde, 1-allylindole-3-carboxaldehyde, 7-azaindole-3-carboxaldehyde, 3-formylindole-2-carboxylate methyl ester, 4-nitroindole-3-carboxaldehyde, 4-bromoindole-3-carboxaldehyde, 5-formyl-2,4-dimethylpyrrole-3-carboxylic acid, and 2-formylpyrrole-1-acetic acid.

The invention need not be limited to the pyrrole nucleus. Other useful commercially available aldehyde containing heterocycles useful in the practice of the invention include various imidazole and pyrazole-based heterocycles, such as 5-methylpyrazole-3-carboxaldehyde, 3-phenylpyrazole-4-carboxaldehyde, 2-methylimidazole-4-carboxaldehyde, 4-methylimidazole-5-carboxaldehyde, imidazole-4-carboxaldehyde, 5-formyluracil, 3-p-methylphenylpyrazole-4-carboxaldehyde, 3-p-hydroxyphenylpyrazole-4-carboxaldehyde, 3-p-methoxyphenylpyrazole-4-carboxaldehyde, 3-p-fluorophenylpyrazole-4-carboxaldehyde, 3-m-fluorophenylpyrazole-4-carboxaldehyde, 5-p-fluorophenylpyrazole-4-carboxaldehyde, 3-p-chlorophenylpyrazole-4-carboxaldehyde, 3-p-trifluoromethylphenylpyrazole-4-carboxaldehyde, 3-(3,4-dimethoxyphenyl)pyrazole-4-carboxaldehyde, 3-(3,5-difluorophenyl)pyrazole-4-carboxaldehyde, 3-t-butylpyrazole-4-carboxaldehyde, 2-butyl-5-chloroimidazole-4-carboxaldehyde, 5-chloro-2-phenylimidazole-4-carboxaldehyde, pyrazole-4-carboxaldehyde, 2-thienylpyrazole-4-carboxaldehyde, indazole-3-carboxaldehyde, 4-methylimidazole-2-carboxaldehyde, and 4-(4-fluorophenyl)imidazole-2-carboxaldehyde.

One skilled in the art will recognize that the exact choice of heterocyclic aldehyde need not be restricted by what is commercially available. For example, a given heteroaromatic nucleus can be readily carbonylated. Thus, aldehyde groups can be introduced into a heteroaromatic skeleton, for example, by 1) metal-catalyzed carbonylation of a heteroaromatic halide or triflate, 2) acid-catalyzed electrophilic acylation of an orthoester or equivalent thereof and similar Friedel-Crafts electrophilic acylation reactions, such as the Reimer-Tiemann reaction of a hydroxy-substituted heteroaromatic or Vilsmeier-Haack reaction, and 3) via carboxylation-reduction of metallated heteroaromatics. Aldehydes have also been introduced into metallated heteroaromatics by quenching with dry N,N-dimethylformamide (DMF).

Compounds of the invention of Formula III contain substituent Q which is an aldehyde or protected aldehyde. In some embodiments, the protected aldehyde is selected from the group consisting of an acetal, an aminal, a dithioacetal (dithiane), a protected hemiaminal, an alkene, and a protected hemithioacetal. Exemplary protecting groups are found in Greene and Wuts supra, Chapter 4. Acetals include acylic acetals, such as dimethyl acetals, dibenzyl acetals, and diacetyl acetals, and cyclic acetals, such as 1,3-dioxanes and 1,3-dioxolanes. Protected or masked versions of an aldehyde can be employed to allow chemical transformations to be performed prior to immobilization on the support. In some embodiments, the protected form of the aldehyde is selected to be removable under conditions suitable for forming the Schiff base, including for example, acid-catalyzed hydrolysis. In some embodiments, the protected aldehyde takes the form of an alkene. In such embodiments, the aldehyde can be revealed by ozonolytic cleavage or by dihydroxylation followed by cleavage of the resultant diol by periodate, for example.

The pyrrole-containing compound of Formula III can be optionally substituted with one or more substituents on the nucleus as represented by group A. In some embodiments, A can be represented by any optional substitution as defined herein above. In some embodiments, A is selected from the group consisting of aryl, hydrogen, hydroxyl, hydroxyalkyl, a $C_1$-$C_4$ straight chain or branched alkyl and alkoxy. In some embodiments, A is another hydroxy group or hydroxyalkyl group which can serve as a second attachment point for a second nucleic acid.

In some embodiments, a compound of Formula III includes W, X, Y, and Z substitution which comprises a fused ring system selected from the group consisting of a benzene, a pyridine, a furan, a thiophene, a pyridazine, a pyrazine, and a pyrimidine. In some embodiments, a compound of Formula III includes W, X, Y, and Z substitution which comprise a fused benzene ring, thus providing an indole nucleus. The chemistry of indoles is well characterized and the requisite aldehyde is readily provided in commercially available indole compounds or easily introduced by carbonylation (formylation). Indeed the direct formylation of indole is well known by the Vilsmeier-Haack reaction (James, P. N.; Snyder, H. R. "Indole-3-aldehyde". *Organic Syntheses* 39:30, (1959)).

The indole nucleus can be readily assembled de novo through the Leimgruber-Batcho or Fischer indole syntheses. Numerous other indole synthesis reactions are known in the art and can be employed to provide substituted indoles. Such reactions include, without limitation the Bartoli indole synthesis, the Bischler-Mohlau indole synthesis, the Fukuyama indole synthesis, the Gassman indole synthesis, the Hemetsberger indole synthesis, the Larock indole synthesis, the Madelung synthesis, the Nenitzescu indole synthesis, the Reissert indole synthesis, and the Baeyer-Emmerling indole synthesis.

In some embodiments, L is a linker selected from a $C_1$-$C_{12}$ alkyl, aralkyl, and aryl, any of which is optionally substituted; wherein one or more methylene unit ($CH_2$) unit of the $C_1$-$C_{12}$ alkyl is optionally replaced by any combination of oxygen, carbonyl(C=O), and NH. The linking unit can be any structure. In some embodiments, the linker can be selected to have generally hydrophobic properties. In some such embodiments, the linker will generally lack, or possess few polar functional groups.

In some embodiments, the linker L can be hydrophilic. In some such embodiments, the linker can incorporate polar functional groups including, without limitation, amides, hydroxyls, amines, and the like. In some embodiments, a hydrophilic linker can be based on an oligopolyethylene glycol structure. In some embodiments, a hydrophilic linker can be based on an oligopolypropylene glycol structure. In some embodiments, a hydrophilic linker can be based on a polyamide structure.

In some embodiments, the linker L can be a cleavable linker, including cleavable azide linkers as disclosed in U.S. Pat. No. 7,592,435, which is incorporated herein by reference in its entirety. Such linkers are based on azide acetals which can be removed by reduction of the azide moiety to an amine with phosphine reagents. The resultant hemiaminal subsequently unravels releasing the bound substrate as shown in the general scheme below.

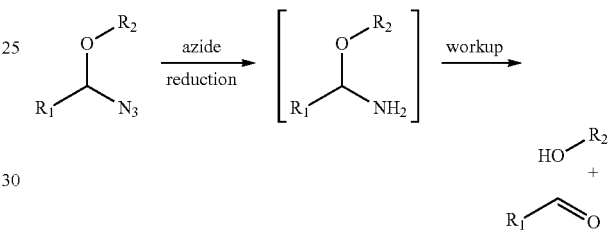

Cleavable linkers have also been developed using photochemical cleavage and other orthogonal chemistries as known in the art, such as the linkers disclosed in U.S. Pat. Nos. 7,785,796 and 7,795,424, and in "Linker Strategies in Solid-Phase Organic Synthesis" Scott, P. Ed., John Wiley & Sons, Chichester, UK (2009), all of which are incorporated herein by reference in their entirety.

In some embodiments, linker L has a linear length in a range from between about 1 to about 15 atoms. In other embodiments, linker L has a linear length in a range from between about 5 to 15 atoms. In yet further embodiments, linker L has a linear length in a range from between about 10 to 15 atoms. In some embodiments, the linker length is at least 2 atoms, at least 3, 4, 5, 6, 7, 8, 9, 10, 11, 12, 13, 14, up to 15 atoms. In some embodiments, the linker length is in a range from between about 15 to 20 atoms. In some embodiments, the linker length is at least 15 atoms, at least 16, 17, 18, 19 up to 20 atoms.

In some embodiments, the compound of Formula III includes substitution where A is hydrogen or methyl, Q is a protected aldehyde, $R_1$ is N-iPr$_2$, and $R_2$ is OCH$_2$CH$_2$CN. In some embodiments, the compound of Formula III includes substitution where A is a hydroxyl, alkoxy or hydroxyalkyl, Q is a protected aldehyde, $R_1$ is N-iPr$_2$, and $R_2$ is OCH$_2$CH$_2$CN. In both such embodiments, the W, X, Y, Z can be the ring fusion as discussed above, including the indole nucleus. As described above, where A is hydroxyl or hydroxyalkyl, the compound can be used for further attachment of a second nucleic acid. One skilled in the art will recognize that such a system would benefit, during synthesis, from the use of appropriate protecting groups to perform nucleic acid conjugation sequentially as needed. Thus, in some embodiments, compounds of formula III also include those with a protecting group on the hydroxyl or hydroxyl alkyl group.

When the phosphorus of compounds of Formula III has $R_1$=N-i$Pr_2$, and $R_2$=OCH$_2$CH$_2$CN, compounds of Formula III are primed for coupling via phosphoramidite coupling chemistry, as known in the art. Phosporamidite coupling chemistry has been employed in the context of solid phase nucleic acid synthesis, for example.

Exemplary compounds of Formula III include the following:

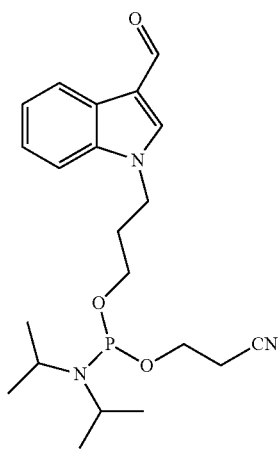

III-A

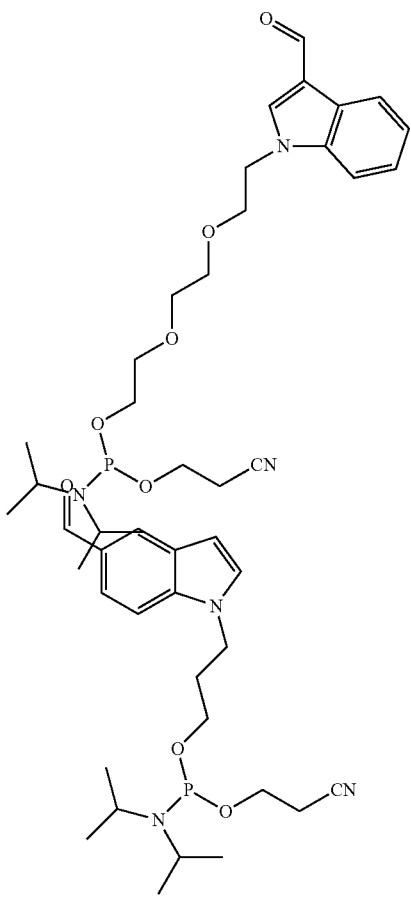

III-B

III-C

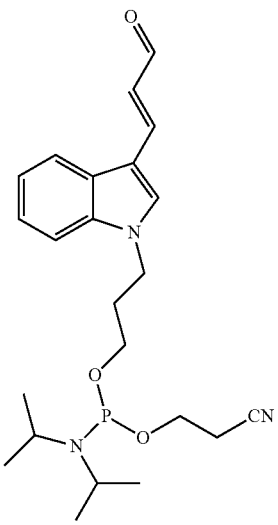

III-D

As described above, compounds of Formula III can be coupled to nucleic acids to provide a compound of Formula IV:

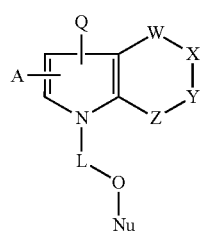

IV wherein, W, X, Y, and Z are independently selected from the group consisting of CH, N, O, S, null, and bond; A is selected from the group consisting of aryl, hydrogen, hydroxyl, alkoxy hydroxyalkyl, and a $C_1$-$C_4$ straight chain or branched alkyl; Q is an aldehyde or protected aldehyde; wherein the bonds between each of W-X, X-Y, and Y-Z are selected from the group consisting of single bond, double bond, a triple bond, and no bond when W, X, Y, or Z is a bond; L is a linker selected from a $C_1$-$C_{12}$ alkyl, aralkyl, and aryl, any of which is optionally substituted; wherein one or more methylene unit (CH$_2$) unit of said $C_1$-$C_{12}$ alkyl is optionally replaced by any combination of oxygen, carbonyl(C=O), and NH; and Nu is a nucleic acid.

In some embodiments, the compound of Formula IV has a structure in which the protected aldehyde is selected from the group consisting of an acetal, an aminal, a dithioacetal, a protected hemiaminal, an alkene, and a protected hemithioacetal. Generally, any protected aldehyde employed at this point prior to immobilization will be the same form as that described for the phosphorus containing precursor of Formula III, although this is not a requirement.

In some embodiments, the compound of Formula IV has a structure in which W, X, Y, and Z comprise a fused ring system selected from the group consisting of a benzene, a pyridine, a furan, a thiophene, a pyridazine, a pyrazine, and a pyrimidine. In some embodiments, the compound of Formula IV has a structure in which W, X, Y, and Z comprise a fused benzene ring.

Compounds of Formula IV represent conjugated nucleic acids that are ready to couple to support via Schiff base chemistry. The preparation of compounds of Formula IV from Formula III is accomplished by standard phosphorus-based nucleic acid coupling chemistry.

In some embodiments, the compound of Formula IV has a structure in which A is hydrogen or methyl, Q is a protected aldehyde, and Nu is selected from the group consisting of a 3'-phosphate-linked nucleic acid, a 3'-thiophosphate-linked nucleic acid, and a 3'-phosphate linked modified nucleic acid. In some embodiments, the compound of Formula IV has a structure in which A is hydrogen or methyl, Q is a protected aldehyde, and Nu is a 5'-phosphate-linked nucleic acid, a 5'-thiophosphate-linked nucleic acid, and a 5'-phosphate linked modified nucleic acid. In some embodiments, the compound of Formula IV has a structure in which A is hydroxyl, alkoxy, or hydroxyalkyl, Q is a protected aldehyde, and Nu is a 3'-phosphate-linked nucleic acid, a 3'-thiophosphate-linked nucleic acid, and a 3'-phosphate linked modified nucleic acid. In some embodiments, the compound of Formula IV has a structure in which A is hydroxyl, alkoxy or hydroxyalkyl, Q is a protected aldehyde, and Nu is a 5'-phosphate-linked nucleic acid, a 5'-thiophosphate-linked nucleic acid, and a 5'-phosphate linked modified nucleic acid. Thus, where compounds of Formula IV display a hydroxyl or hydroxyalkyl group, further nucleic acid attachment to the heterocyclic core can be achieved. In some such embodiments, this further attachment is via the 3'-linkage, while in other embodiments, attachment is via the 5' linkage. In either such embodiments, the linkage can be through the naturally occurring phosphate linkage, or through any other modified phosphate backbone, including a thiophosphate, for example.

In some embodiments, compounds of Formula IV include the following subgeneric structures where L is any linker as defined herein and Nu is a nucleic acid, also as defined herein.

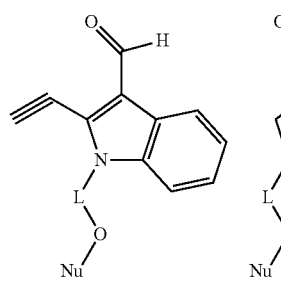 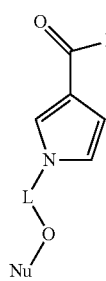 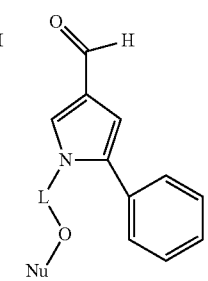

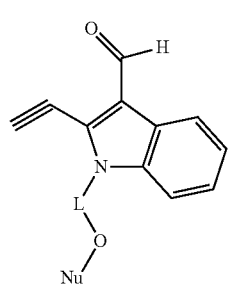 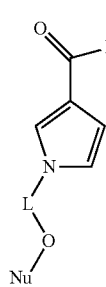 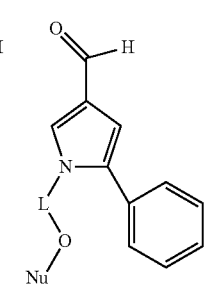

-continued

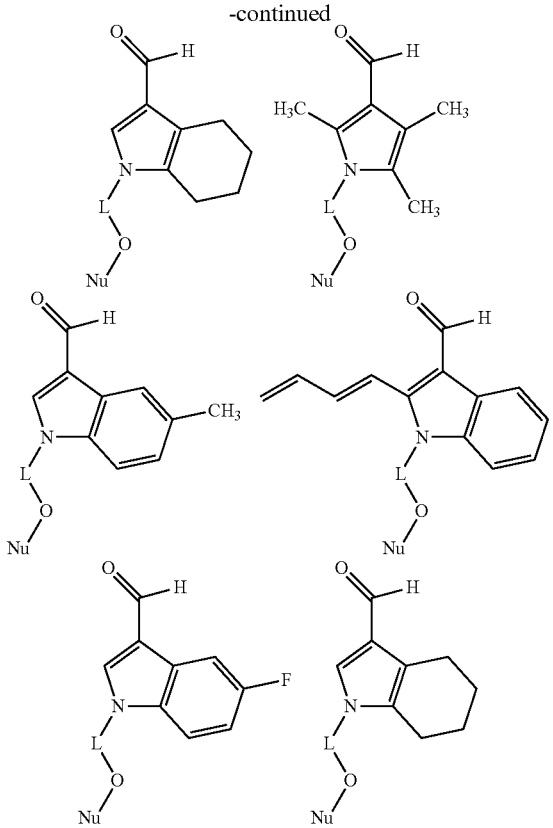

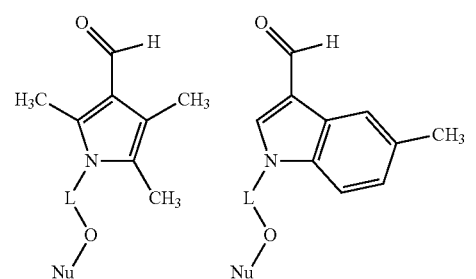

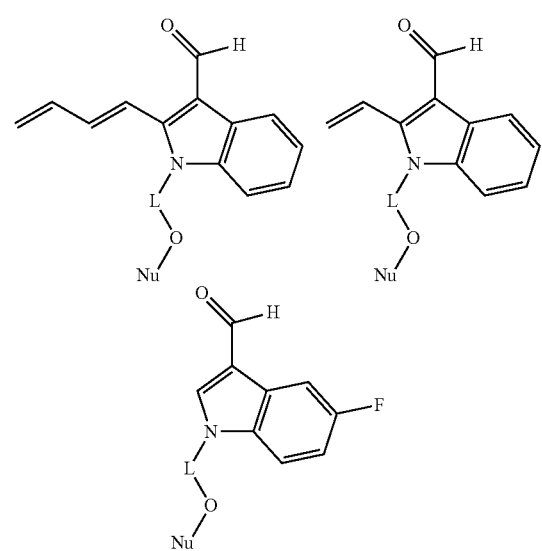

In some embodiments, the present invention provides a support-bound nucleic acid of Formula V:

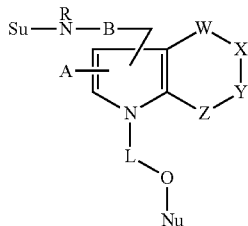

V wherein, W, X, Y, and Z are independently selected from the group consisting of CH, N, O, S, null, and bond; A is selected from the group consisting of aryl, hydrogen, hydroxyl, alkoxy hydroxyalkyl, and a $C_1$-$C_4$ straight chain or branched alkyl; Q is an aldehyde or protected aldehyde; wherein the bonds between each of W-X, X-Y, and Y-Z are selected from the group consisting of single bond, double bond, a triple bond, and no bond when W, X, Y, or Z is a bond; L is a linker selected from a $C_1$-$C_{12}$ alkyl, aralkyl, and aryl, any of which is optionally substituted; wherein one or more methylene unit ($CH_2$) unit of said $C_1$-$C_{12}$ alkyl is optionally replaced by any combination of oxygen, carbonyl(C=O), and NH; Nu is a nucleic acid; Su is a support material; and B is a single or double bond, such that when B is a single bond, R is hydrogen and when B is a double bond R is null.

In some embodiments, the support-bound nucleic acid has a structure in which W, X, Y, and Z comprise a fused ring system selected from the group consisting of a benzene, a pyridine, a furan, a thiophene, a pyridazine, a pyrazine, and a pyrimidine. In some embodiments, the support-bound nucleic acid has a structure in which W, X, Y, and Z comprise a fused benzene ring. In some embodiments, the support-bound nucleic acid has a structure in which A is hydrogen or methyl, Q is a protected aldehyde, and Nu is selected from the group consisting of a 3'-phosphate-linked nucleic acid, a 3'-thiophosphate-linked nucleic acid, and a 3'-phosphate linked modified nucleic acid. In some embodiments, the support-bound nucleic acid has a structure in which A is hydrogen or methyl, Q is a protected aldehyde, Nu is a 5'-phosphate-linked nucleic acid, a 5'-thiophosphate-linked nucleic acid, and a 5'-phosphate linked modified nucleic acid. In some embodiments, the support-bound nucleic acid has a structure in which A is hydroxyl, alkoxy, or hydroxyalkyl, Q is a protected aldehyde, and Nu is a 3'-phosphate-linked nucleic acid, a 3'-thiophosphate-linked nucleic acid, and a 3'-phosphate linked modified nucleic acid. In some embodiments, the support-bound nucleic acid has a structure in which A is hydroxyl, alkoxy or hydroxyalkyl, Q is a protected aldehyde, and Nu is a 5'-phosphate-linked nucleic acid, a 5'-thiophosphate-linked nucleic acid, and a 5'-phosphate linked modified nucleic acid.

In some embodiments, the support-bound nucleic acid has a structure in which the support material is selected from a silica bead, CPG glass, a polymer bead, a microfluidic cell, and a 96 well plate. In some embodiments, the support-bound nucleic acid has a structure in which the support includes a polymer bead including a polymer selected from the group consisting of polystyrene, agarose, polyacrylate, and polyacrylamide. In some embodiments, the support employed is a fused silica structure which can be of any geometry, including nominally spherical, oblong pill-shaped, or the like. In some embodiments, the support can include a magnetic core. In some such embodiments, the support can be a glass coated iron particle, or other magnetic material. In other embodiments, the support can be a dextran coated iron particle, or other magnetic material.

In some embodiments, the present invention provides a method of immobilizing a nucleic acid comprising forming a Schiff-base product by reaction of a compound of Formula IV:

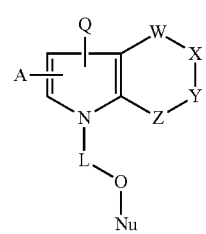

IV wherein, W, X, Y, and Z are independently selected from the group consisting of CH, N, O, S, null, and bond; A is selected from the group consisting of aryl, hydrogen, hydroxyl, alkoxy hydroxyalkyl, and a $C_1$-$C_4$ straight chain or branched alkyl; Q is an aldehyde or protected aldehyde; wherein the bonds between each of W-X, X-Y, and Y-Z are selected from the group consisting of single bond, double bond, a triple bond, and no bond when W, X, Y, or Z is a bond; L is a linker selected from a $C_1$-$C_{12}$ alkyl, aralkyl, and aryl, any of which is optionally substituted; wherein one or more methylene unit ($CH_2$) unit of said $C_1$-$C_{12}$ alkyl is optionally replaced by any combination of oxygen, carbonyl(C=O), and NH; and Nu is a nucleic acid; with a support material displaying an amino or masked amino functional group.

In some embodiments, the method of invention is carried with a structure of Formula IV in which W, X, Y, and Z comprise a fused ring system selected from the group consisting of a benzene, a pyridine, a furan, a thiophene, a pyridazine, a pyrazine, and a pyrimidine. In some embodiments, the method of invention is carried with a structure of Formula IV in which W, X, Y, and Z comprise a fused benzene ring.

In some embodiments, the method of invention is carried with a structure of Formula IV in which A is hydrogen or methyl, Q is a protected aldehyde, Nu is selected from the group consisting of a 3'-phosphate-linked nucleic acid, a 3'-thiophosphate-linked nucleic acid, and a 3'-phosphate linked modified nucleic acid. In some embodiments, the method of invention is carried with a structure of Formula IV in which A is hydrogen or methyl, Q is a protected aldehyde, Nu is a 5'-phosphate-linked nucleic acid, a 5'-thiophosphate-linked nucleic acid, and a 5'-phosphate linked modified nucleic acid. In some embodiments, the method of invention is carried with a structure of Formula IV in which A is hydroxyl, alkoxy, or hydroxyalkyl, Q is a protected aldehyde, and Nu is a 3'-phosphate-linked nucleic acid, a 3'-thiophosphate-linked nucleic acid, and a 3'-phosphate linked modified nucleic acid. In some embodiments, the method of invention is carried with a structure of Formula IV in which A is hydroxyl, alkoxy or hydroxyalkyl, Q is a protected aldehyde, and Nu is a 5'-phosphate-linked nucleic acid, a 5'-thiophosphate-linked nucleic acid, and a 5'-phosphate linked modified nucleic acid.

In some embodiments, the method of invention is carried with a support material is selected from a silica bead, CPG glass, a polymer bead, a microfluidic cell, and a 96 well plate.

In some embodiments, the method of invention is carried with a polymer bead that includes a polymer selected from the group consisting of polystyrene, agarose, polyacrylate, and polyacrylamide.

In some embodiments, the method of invention is carried with a support material that an amino or masked amino functional group is selected from the group consisting of an amine, a hydrazine, an acylhydrazine, a semicarbazide, an aminooxy, a hydrazone, an imine, and an enamine. In some such embodiments, masked amino functional groups include those which will release an amino group upon exposure to conditions suitable for the Schiff base chemistry, including hydrazones, imines, enamines, and the like. For example, the reaction to immobilize compounds of Formula IV can include Schiff base exchange. The general Schiff base reaction is shown by the general scheme below.

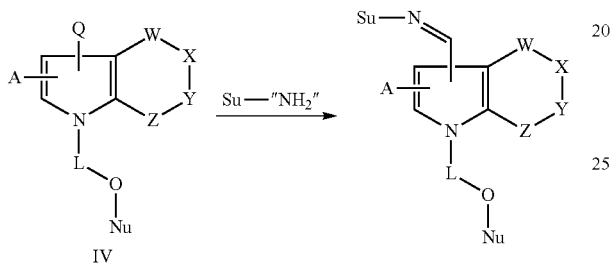

As shown in the scheme above, the aldehyde or masked aldehyde is given by Q and the Support, Su, is provided with an amino group or the aforementioned masked amino groups. In some embodiments, the masked amino functional group is an imine or enamine and the conditions for forming the Schiff base are sufficient to unravel the imine or enamine and allow for subsequent Schiff base formation with compounds of Formula IV.

The aldehyde or masked aldehyde coupling partner Q in Formula IV couples to the unveiled amino group on the support. In some such embodiments, both the amino group of the support and the masked aldehyde Q are both unveiled under conditions suitable for Schiff base formation. One skilled in the art will recognize that any combination of masked amino or masked aldehyde can be used with either an unmasked amino group or unmasked aldehyde. Thus, methods of the invention can include reaction under Schiff base forming conditions with a masked amino group and an unmasked aldehyde. Methods of the invention can also include reaction under Schiff base forming conditions with an unmasked amino group and a masked aldehyde.

In some embodiments, Schiff base forming conditions can include acid catalysis and a means for azeotropic removal of water. In some embodiments, Schiff base conditions can include acid catalysis and a means for trapping or removing the released masking group. In some embodiments, Schiff base forming conditions can include simple acid catalysis. In some embodiments, Schiff base forming conditions can include the use of a protic solvent with or without acid catalysis.

In some embodiments, methods of the invention further include reduction of the Schiff base. In some embodiments, reduction can be performed as a separate step after Schiff base imine formation using any reducing agent employed in the art. For example, sodium borohydride or sodium cyanoborohydride. In some embodiments reduction can be performed in "one pot" along with Schiff base formation, such as with the use of sodium cyanoborohydride.

It is understood that modifications which do not substantially affect the activity of the various embodiments of this invention are also provided within the definition of the invention provided herein. Accordingly, the following examples are intended to illustrate but not limit the present invention.

Example I

2-Cyanoethyl (3-(3-formyl-1H-indol-1-yl)propyl) diisopropylphosphoramidite III-A This Example shows the preparation of phosphoramidite III-A Synthesis of Indole-3-Aldehyde

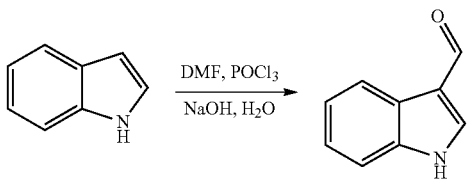 [SMILES: c1ccc2[nH]ccc2c1 ; O=Cc1c[nH]c2ccccc12]

Reference: Philip N. James and H. R. Snyder. *Organic Syntheses*, 1963, 4, 539.

In a 1-L round-bottomed, three-necked flask fitted with an efficient mechanical stirrer, a drying tube containing Drierite, and a 125-mL dropping funnel is placed 288 mL (274 g, 3.74 moles) of freshly distilled dimethylformamide. The flask and its contents are cooled in an ice-salt bath for about 0.5 hour, and 86 mL (144 g, 0.94 mole) of freshly distilled phosphorus oxychloride is subsequently added with stirring to the dimethylformamide over a period of 0.5 hour. The pinkish color of the formylation complex may be observed during this step. The 125-mL dropping funnel is replaced with a 200-mL dropping funnel, and a solution of 100 g. (0.85 mole) of indole in 100 mL (95 g, 1.3 moles) of dimethylformamide is added to the yellow solution over a period of 1 hour during which time the temperature should not rise above 10° C. Once the solution is well mixed, the dropping funnel is replaced with a thermometer, and the temperature of the viscous solution is brought to 35° C. The syrup is stirred efficiently at this temperature for 1 hour, or for 15 minutes longer than is necessary for the clear yellow solution to become an opaque, canary-yellow paste. At the end of the reaction period, 300 g. of crushed ice is added to the paste with careful stirring, producing a clear, cherry-red aqueous solution.

This solution is transferred with 100 mL of water to a 3-L three-necked flask containing 200 g. of crushed ice and fitted with an efficient mechanical stirrer and a separatory funnel containing a solution of 375 g. (9.4 moles) of sodium hydroxide in 1 L of water. The aqueous base is added dropwise with stirring until about one-third of it has been added. The remaining two-thirds is added rapidly with efficient stirring, and the resulting suspension is heated rapidly to the boiling point and allowed to cool to room temperature, after which it is placed in a refrigerator overnight. The precipitate is collected on a filter and resuspended in 1 L of water. Most of the inorganic material dissolves, and the product is then collected on a filter, washed with three 300-mL portions of water and air-dried, yielding about 120 g. (97%) of indole-3-aldehyde, m.p. 196-197° C. The indole-3-aldehyde resulting from this procedure

Synthesis of 1-(3-Hydroxypropyl)-1H-indole-3-carbaldehyde

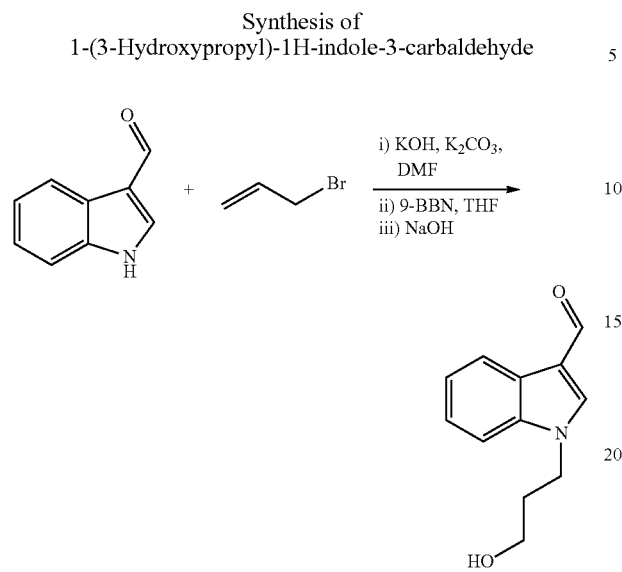

Reference: Magdy A. H. Zahran and Atef M. Ibrahim. *J. Chem. Sci.,* 2009, 121(4), 455-462.

In a 10 mL Pyrex-glass vessel is mixed indole-3-carboxaldehyde (145 mg, 1 mmol), allylbromide (121 mg, 1 mmol), KOH (224 mg, 4 mmol) and anhydrous K$_2$CO$_3$ (553 mg, 4 mmol) in 1 mL DMF. This mixture is subjected to microwave irradiation at 350 W in successive 30 s periods, with 30 s periods at room temperature between each irradiation to avoid overheating the reaction. After the reaction has reached completion as monitored by TLC (5:1-hexanes:EtOAc) the reaction mixture is allowed to cool to room temperature and then is poured into 25 mL water. The precipitated solids are removed by filtration and washed 3×25 mL with water. The resulting solids are dried under vacuum and then recrystallized from ethanol to afford colorless crystals.

Reference: Soderquist, J. A. and Brown, H. C. *J. Org. Chem.* 1981, 46, 4599.

In a 10 mL round-bottom flask, 1-Allyl-1H-indole-3-carbaldehyde (169 mg, 0.91 mmol) is dissolved in 0.5 mL of anhydrous THF. To this solution is added 0.5 M of 9-BBN in THF (2 mL, 1.0 mmol). The reaction is allowed to stir at room temperature for 1 hr, whereupon a 1 M solution of NaOH (2.5 mL) is added. The organic layer is diluted with 10 mL of diethyl ether and the aqueous layer is removed. The organic layer is washed 3×10 mL with 1 M NaOH, followed by 2×10 mL water and 2×10 mL saturated NaCl solutions. The organic layer is then dried over Na$_2$SO$_4$ and the solvent is removed under reduced pressure to afford 1-(3-hydroxypropyl)-1H-indole-3-carbaldehyde.

Synthesis of 2-Cyanoethyl (3-(3-formyl-1H-indol-1-yl)propyl)diisopropylphosphoramidite III-A

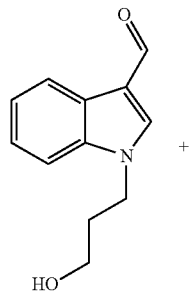

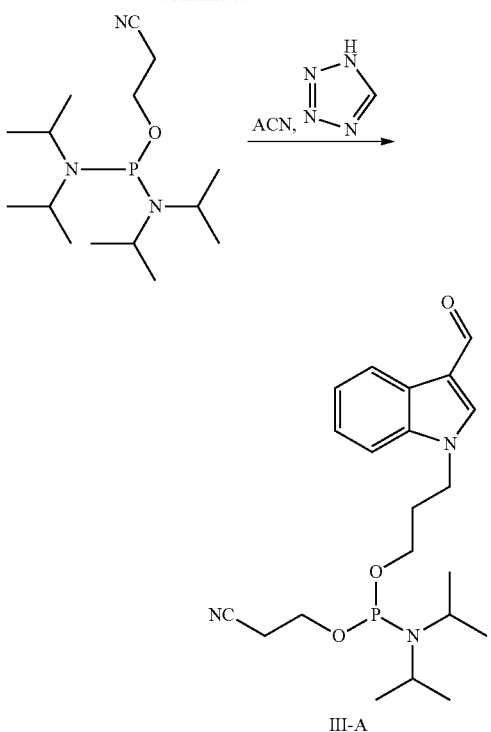

III-A

Reference: John Nielsen, Michael Taagaard, John E. Marugg, Jacques H. van Boom, and Otto Dahl, *Nucleic Acids Research,* 1986, 14(18), 7391-7403.

1-(3-Hydroxypropyl)-1H-indole-3-carbaldehyde (0.5 g, 2.46 mmol) is dried by coevaporation with anhydrous acetonitrile (3 mL) and dissolved into dry acetonitrile (2.5 mL) under nitrogen. A solution of tetrazole (165 mg, 2.36 mmol) in dry acetonitrile (0.40 M) is added with stirring at 20° C., followed by 2-cyanoethyl-N,N,N',N'-tetraisopropylphosphoramidite (704 mg, 2.33 mmol). After stirring for 1 hr, the precipitate of diisopropyl ammonium tetrazolide is removed by filtration and the solution is diluted with dry acetonitrile to yield a 0.1 M solution of the desired phosphoramidite. This material is not isolated but rather retained as a 0.1 M solution and used as required in this form.

Example II

2-Cyanoethyl (2-(2-(2-(3-formyl-1H-indol-1-yl)ethoxy)ethoxy)ethyl)diisopropylphosphoramidite III-B This Example shows the preparation of phosphoramidite III-B

Synthesis of 2-[2-(2-Triphenylmethoxyethoxyl)ethoxy]ethanol

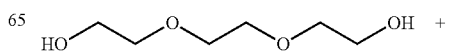

Reference: Kristin Wiederholt and Larry W. McLaughlin, *Nucleic Acids Research*, 1999, 27(12), 2487-2493.

To an ice-cold solution of 7.9 g (52.6 mmol) of tri(ethyleneglycol) in 200 mL anhydrous pyridine is added 4.36 g (15.6 mmol) of triphenyl methyl chloride with a catalytic amount of dimethylamino pyridine. The reaction is allowed to warm to room temperature and stir for 16 hours. The pyridine is then evaporated and the mixture is suspended in 150 mL dichloromethane and extracted 3×150 mL saturated NaHCO$_3$, and then dried over anhydrous Na$_2$SO$_4$. The crude product is isolated as an orange oil, which is subsequently purified via column chromatography on silica gel, eluting with 1:1-hexanes:ethyl acetate.

Synthesis of 2-(2-Triphenylmethoxyethoxyl)ethoxy-1-bromo-ethane

Reference: Kristin Wiederholt and Larry W. McLaughlin, *Nucleic Acids Research*, 1999, 27(12), 2487-2493.

A solution of carbon tetrabromide (8.3 g, 25 mmol) and 10 g of 2-[2-(2-triphenylmethoxyethoxy)ethoxy]ethanol are stirred together in 75 mL dichloromethane at 0° C. To this solution is added a solution of 6.7 g triphenylphosphine (25 mmol) in 75 mL dichloromethane dropwise over 1½ hours at 0° C. After stirring for an additional 2 hours, the solution is evaporated to dryness and the residual solids are resuspended in 150 mL diethyl ether. The triphenylphosphine by-product is removed via vacuum filtration and the product is then purified via column chromatography over silica gel, eluting with dichloromethane.

Synthesis of 1-(2-(2-(2-Triphenylmethoxyethoxyl)ethoxy)ethyl)-1H-indole-3-carbaldehyde Reference: Kristin Wiederholt and Larry W. McLaughlin, *Nucleic Acids Research*, 1999, 27(12), 2487-2493.

To 1.01 g of indole-3-carboxyaldehyde (6.95 mmol) dissolved in 250 mL THF is added 0.28 g of sodium hydride (11 mmol). After heating the reaction to reflux for 3 hours under nitrogen, 5.0 g of 2-(2-triphenylmethoxyethoxy)ethoxy-1-bromo-ethane (11 mmol) is added. The reaction is allowed to reflux for an additional 16 hours, monitoring by TLC (9:1-ethyl acetate:dichloromethane on alumina). Upon complete consumption of the indole-3-carboxyaldehyde, the reaction is quenched via addition of 25 mL MeOH and the solvent is

Synthesis of 1-(2-(2-(2-Hydroxyethoxy)ethoxy)ethyl)-1H-indole-3-carbaldehyde

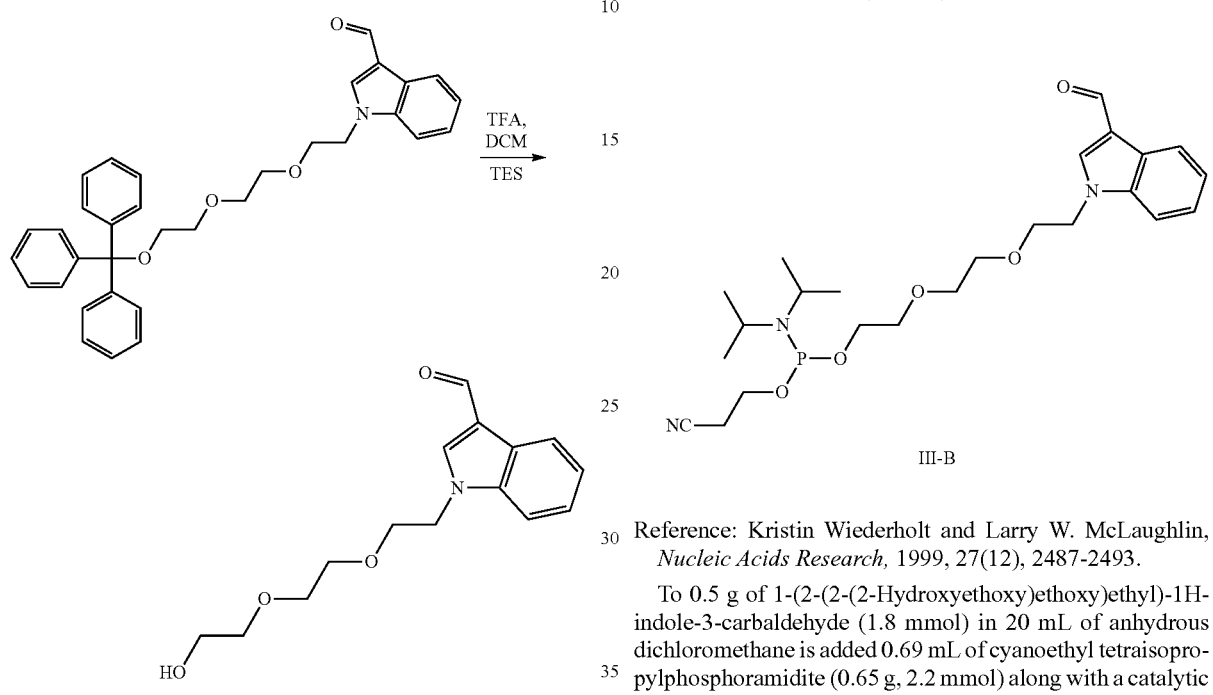

Reference: Kristin Wiederholt and Larry W. McLaughlin, *Nucleic Acids Research*, 1999, 27(12), 2487-2493.

To 2.6 g of 1-(2-(2-(2-triphenylmethoxyethoxy)ethoxy)ethyl)-1H-indole-3-carbaldehyde (5.0 mmol) in 50 mL dichloromethane is added 4.0 mL of triethylsilane (2.9 g, 25 mmol) followed by 4.0 mL of trifluoroacetic acid (5.5 g, 50 mmol). The solution is stirred at room temperature for 2 hrs and then washed 3×100 mL saturated NH$_4$CO$_3$. The solution is dried over anhydrous Na$_2$SO$_4$ and the solvent is removed via vacuum. The resultant residue is purified via column chromatography over alumina, eluting with a gradient of methanol in dichloromethane.

Synthesis of 2-Cyanoethyl (2-(2-(2-(3-formyl-1H-indol-1-yl)ethoxy)ethoxy)ethyl)diisopropylphosphoramidite

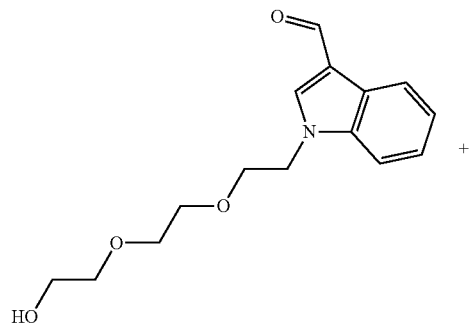

Reference: Kristin Wiederholt and Larry W. McLaughlin, *Nucleic Acids Research*, 1999, 27(12), 2487-2493.

To 0.5 g of 1-(2-(2-(2-Hydroxyethoxy)ethoxy)ethyl)-1H-indole-3-carbaldehyde (1.8 mmol) in 20 mL of anhydrous dichloromethane is added 0.69 mL of cyanoethyl tetraisopropylphosphoramidite (0.65 g, 2.2 mmol) along with a catalytic amount of tetrazole. The reaction is stirred for 30 minutes while monitoring by TLC (alumina in methanol:dichloromethane, 1:99). Once the reaction is judged complete based on the disappearance of starting material by TLC, the crude reaction mixture is filtered to remove any precipitated diisopropyl ammonium tetrazolide. The crude filtered solution is then loaded onto an alumina column and purified by column chromatography, eluting with dichloromethane and a trace of methanol to yield the title compound III-B.

Example III

2-Cyanoethyl (3-(5-formyl-1H-indol-1-yl)propyl) diisopropylphosphoramidite III-C This Example shows the preparation of phosphoramidite

Synthesis of 1-(3-Hydroxypropyl)-1H-indole-5-carbaldehyde

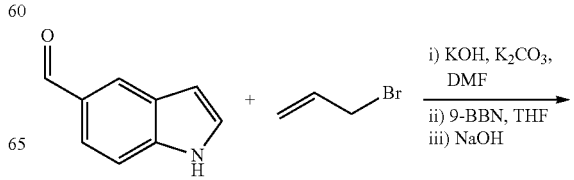

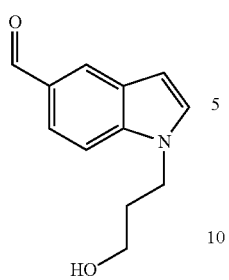

Reference: Magdy A. H. Zahran and Atef M. Ibrahim. *J. Chem. Sci.*, 2009, 121(4), 455-462.

In a 10 mL Pyrex-glass vessel is mixed indole-5-carboxaldehyde (145 mg, 1 mmol), allylbromide (121 mg, 1 mmol), KOH (224 mg, 4 mmol) and anhydrous $K_2CO_3$ (553 mg, 4 mmol) in 1 mL DMF. This mixture is subjected to microwave irradiation at 350 W in successive 30 s periods, with 30 s periods at room temperature between each irradiation to avoid overheating the reaction. After the reaction has reached completion as monitored by TLC (5:1-hexanes:EtOAc) the reaction mixture is allowed to cool to room temperature and then is poured into 25 mL water. The precipitated solids are removed by filtration and washed 3×25 mL with water. The resulting solids are dried under vacuum and then recrystallized from ethanol to afford colorless crystals.

Reference: Soderquist, J. A. and Brown, H. C. *J. Org. Chem.* 1981, 46, 4599.

In a 10 mL round-bottom flask, 1-Allyl-1H-indole-5-carbaldehyde (169 mg, 0.91 mmol) is dissolved in 0.5 mL of anhydrous THF. To this solution is added 0.5 M of 9-BBN in THF (2 mL, 1.0 mmol). The reaction is allowed to stir at room temperature for 1 hr, whereupon a 1 M solution of NaOH (2.5 mL) is added. The organic layer is diluted with 10 mL of diethyl ether and the aqueous layer is removed. The organic layer is washed 3×10 mL with 1 M NaOH, followed by 2×10 mL water and 2×10 mL saturated NaCl solutions. The organic layer is then dried over $Na_2SO_4$ and the solvent is removed under reduced pressure to afford 1-(3-hydroxypropyl)-1H-indole-5-carbaldehyde.

Synthesis of 2-Cyanoethyl (3-(5-formyl-1H-indol-1-yl)propyl)diisopropylphosphoramidite III-C

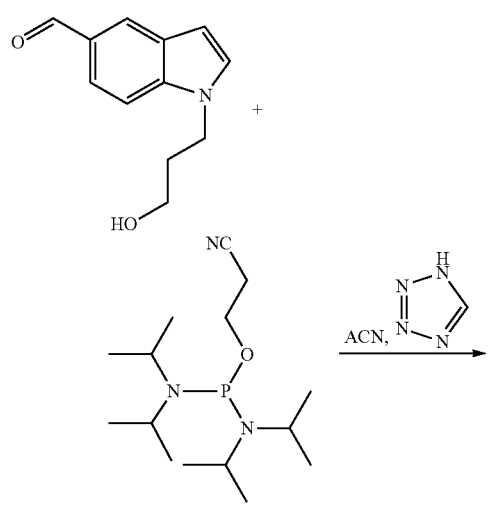

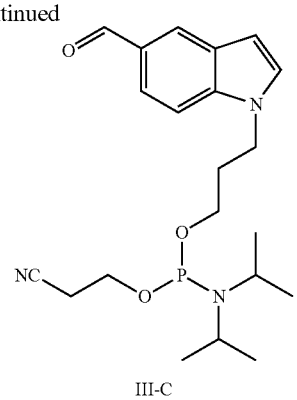

III-C

Reference: John Nielsen, Michael Taagaard, John E. Marugg, Jacques H. van Boom, and Otto Dahl, *Nucleic Acids Research*, 1986, 14(18), 7391-7403.

1-(3-Hydroxypropyl)-1H-indole-5-carbaldehyde (0.5 g, 2.46 mmol) is dried by coevaporation with anhydrous acetonitrile (3 mL) and dissolved into dry acetonitrile (2.5 mL) under nitrogen. A solution of tetrazole (165 mg, 2.36 mmol) in dry acetonitrile (0.40 M) is added with stirring at 20° C., followed by 2-cyanoethyl-N,N,N',N'-tetraisopropylphosphoramidite (704 mg, 2.33 mmol). After stirring for 1 hr, the precipitate of diisopropyl ammonium tetrazolide is removed by filtration and the solution is diluted with dry acetonitrile to yield a 0.1 M solution of the desired phosphoramidite. This material is not isolated but rather retained as a 0.1 M solution and used as required in this form.

Example IV

2-Cyanoethyl (3-(5-formyl-1H-indol-1-yl)propyl) diisopropylphosphoramidite III-D This Example shows the preparation of phosphoramidite III-D Synthesis of 3-(1H-indol-3-yl)acrylaldehyde

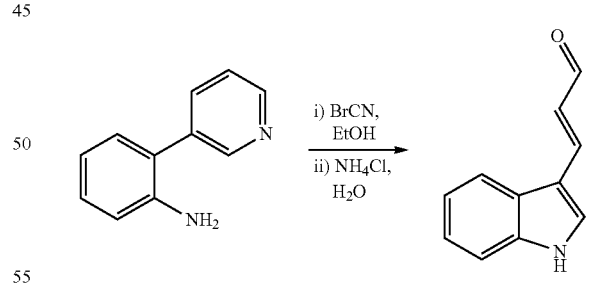

Reference: Aaron M. Kearney, Christopher D. Vanderwal *Angew. Chem. Int. Ed.* 2006, 45, 7803-7806.

To a solution of 10.0 g of 2-(pyridin-3-yl)aniline (58.7 mmol) in 100 mL ethanol is slowly added 6.2 mL of cyanogen bromide (12.4 g, 118 mmol). The reaction is heated to reflux for 1 hour, monitoring by TLC (silica, hexanes:ethyl acetate 1:1) for formation of the Zincke salt. The reaction is then quenched via addition of 50 mL saturated $NH_4Cl$, and extracted with 3×50 mL dichloromethane. The combined organic layers are washed 3×100 mL saturated $NH_4Cl$, followed by drying over anhydrous $Na_2SO_4$ and removal of the

Synthesis of 3-(1-(3-Hydroxypropyl)-1H-indol-3-yl)acrylaldehyde

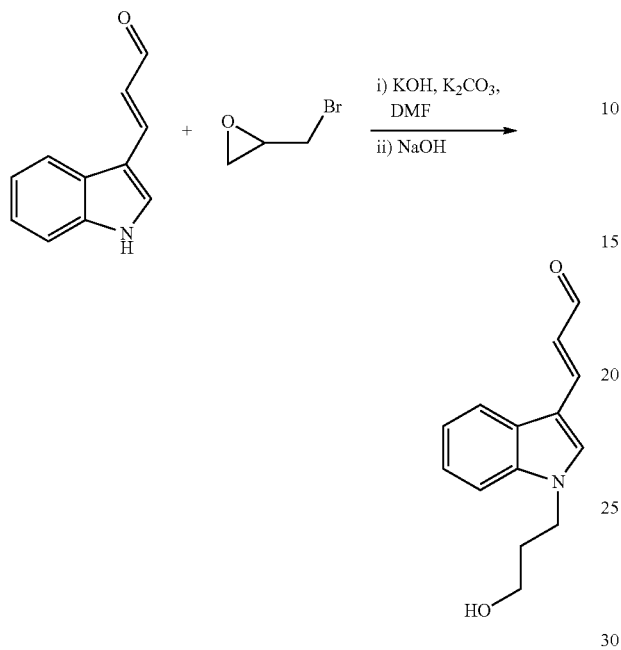

Reference: Peter Nicholl Green, Maurice Shapero, Catherine Wilson *J Med Chem* 1969, 12(2), 326-329

In a 10 mL Pyrex-glass vessel is mixed 3-(1H-indol-3-yl)acrylaldehyde (171 mg, 1 mmol), epibromohydrin (137 mg, 1 mmol), KOH (224 mg, 4 mmol) and anhydrous $K_2CO_3$ (553 mg, 4 mmol) in 1 mL DMF. This mixture is subjected to microwave irradiation at 350 W in successive 30 s periods, with 30 s periods at room temperature between each irradiation to avoid overheating the reaction. After the reaction has reached completion as monitored by TLC (5:1-hexanes:EtOAc) the reaction mixture is allowed to cool to room temperature and then is quenched by the addition of 10 mL 1M NaOH under vigorous stirring. The mixture is stirred for an additional 2 hrs, whereupon it is poured into 50 mL of ice-cold water. The precipitated solids are removed by filtration and washed 3×25 mL with water. The resulting solids are dried under vacuum and then recrystallized from ethanol to afford colorless crystals.

Synthesis of 2-Cyanoethyl (3-(3-(3-oxoprop-1-en-1-yl)-1H-indol-1-yl)propyl)diisopropylphosphoramidite III-D

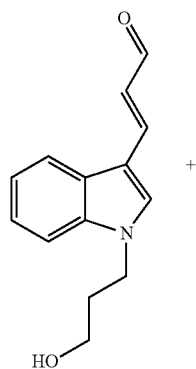

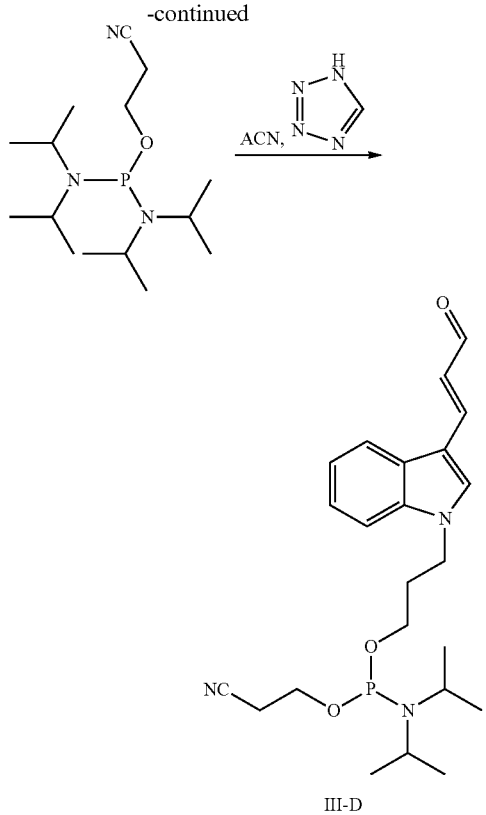

Reference: John Nielsen, Michael Taagaard, John E. Marugg, Jacques H. van Boom, and Otto Dahl, *Nucleic Acids Research*, 1986, 14(18), 7391-7403.

3-(1-(3-Hydroxypropyl)-1H-indol-3-yl)acrylaldehyde (0.56 g, 2.46 mmol) is dried by coevaporation with anhydrous acetonitrile (3 mL) and dissolved into dry acetonitrile (2.5 mL) under nitrogen. A solution of tetrazole (165 mg, 2.36 mmol) in dry acetonitrile (0.40 M) is added with stirring at 20° C., followed by 2-cyanoethyl-N,N,N',N'-tetraisopropylphosphoramidite (704 mg, 2.33 mmol). After stirring for 1 hr, the precipitate of diisopropyl ammonium tetrazolide is removed by filtration and the solution is diluted with dry acetonitrile to yield a 0.1 M solution of the desired phosphoramidite. This material is not isolated but rather retained as a 0.1 M solution and used as required in this form.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A compound of Formula:

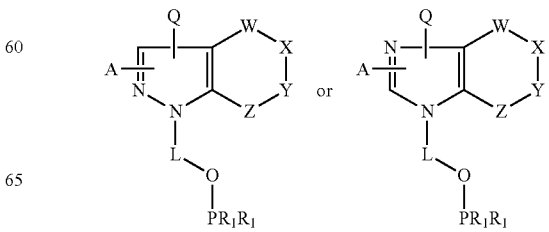

wherein,
W, X, Y, and Z are null, or W, X, Y, and Z comprise a fused benzene ring;
A is selected from the group consisting of aryl, heteroaryl, hydrogen, a $C_1$-$C_4$ alkyl, and halogen;
Q is an aldehyde or protected aldehyde;
L is a linker selected from a $C_1$-$C_{12}$ alkyl, aralkyl, and aryl, any of which is optionally substituted; wherein one or more methylene unit ($CH_2$) of said $C_1$-$C_{12}$ alkyl is optionally replaced by any combination of oxygen, carbonyl(C=O), and NH; and
$R_1$ and $R_2$ are independently selected from the group consisting of —$NR_3R_4$, halogen, $C_1$-$C_8$ alkoxy, aralkoxy, alkenyloxy, alkynyloxy, and $OCH_2CH_2CN$;
wherein $R_3$ and $R_4$ are independently a $C_1$-$C_4$, straight chain or branched alkyl group.

2. The compound of claim 1, wherein the protected aldehyde is selected from the group consisting of an acetal, an aminal, a dithioacetal, a protected hemiaminal, an alkene, and a protected hemithioacetal.

3. The compound of claim 1, wherein A is hydrogen or methyl, Q is a protected aldehyde, $R_1$ is N-$iPr_2$, and $R_2$ is $OCH_2CH_2CN$.

4. The compound of claim 1, wherein A is a phenyl, Q is a protected aldehyde, $R_1$ is N-$iPr_2$, and $R_2$ is $OCH_2CH_2CN$.

5. A compound of Formula:

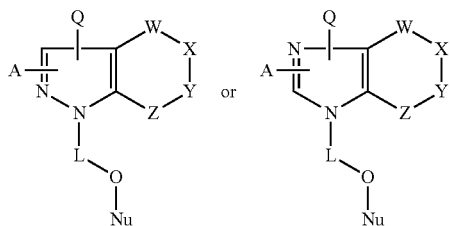

wherein,
W, X, Y, and Z are null, or W, X, Y, and Z comprise a fused benzene;
A is selected from the group consisting of aryl, heteroaryl, hydrogen, a $C_1$-$C_4$ alkyl, and halogen;
Q is an aldehyde or protected aldehyde;
L is a linker selected from a $C_1$-$C_{12}$ alkyl, aralkyl, and aryl, any of which is optionally substituted; wherein one or more methylene unit ($CH_2$) of said $C_1$-$C_{12}$ alkyl is optionally replaced by any combination of oxygen, carbonyl(C=O), and NH; and
Nu is a nucleic acid.

6. The compound of claim 5, wherein the protected aldehyde is selected from the group consisting of an acetal, an aminal, a dithioacetal, a protected hemiaminal, an alkene, and a protected hemithioacetal.

7. The compound of claim 5, wherein A is hydrogen or methyl, Q is a protected aldehyde, Nu is selected from the group consisting of a 3'-phosphate-linked nucleic acid, a 3'-thiophosphate-linked nucleic acid, and a 3'-phosphate linked modified nucleic acid.

8. The compound of claim 5, wherein A is hydrogen or methyl, Q is a protected aldehyde, Nu is selected from the group consisting of a 5'-phosphate-linked nucleic acid, a 5'-thiophosphate-linked nucleic acid, and a 5'-phosphate linked modified nucleic acid.

9. The compound of claim 5, wherein A is phenyl, Q is a protected aldehyde, and Nu is selected from the group consisting of a 3'-phosphate-linked nucleic acid, a 3'-thiophosphate-linked nucleic acid, and a 3'-phosphate linked modified nucleic acid.

10. The compound of claim 5, wherein A is phenyl, Q is a protected aldehyde, and Nu is selected from a group consisting of a 5'-phosphate-linked nucleic acid, a 5'-thiophosphate-linked nucleic acid, and a 5'-phosphate linked modified nucleic acid.

11. A support-bound nucleic acid of Formula:

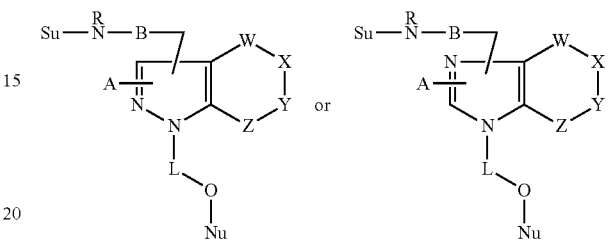

wherein,
W, X, Y, and Z are null, or W, X, Y, and Z comprise a fused benzene ring;
A is selected from the group consisting of aryl, heteroaryl, hydrogen, a $C_1$-$C_4$ alkyl, and halogen;
L is a linker selected from a $C_1$-$C_{12}$ alkyl, aralkyl, and aryl, any of which is optionally substituted; wherein one or more methylene unit ($CH_2$) of said $C_1$-$C_{12}$ alkyl is optionally replaced by any combination of oxygen, carbonyl(C=O), and NH;
Nu is a nucleic acid;
Su is a support material; and
B is a single or double bond, such that when B is a single bond, R is hydrogen and when B is a double bond ft is null.

12. The support-bound nucleic acid of claim 11, wherein A is hydrogen or methyl, Nu is selected from the group consisting of a 3'-phosphate-linked nucleic acid, a 3'-thiophosphate-linked nucleic acid, and a 3'-phosphate linked modified nucleic acid.

13. The support-bound nucleic acid of claim 11, wherein A is hydrogen or methyl, Nu is selected from the group consisting of a 5'-phosphate-linked nucleic acid, a 5'-thiophosphate-linked nucleic acid, and a 5'-phosphate linked modified nucleic acid.

14. The support-bound nucleic acid of claim 11, wherein A is phenyl, and Nu is selected from the group consisting of a 3'-phosphate-linked nucleic acid, a 3'-thiophosphate-linked nucleic acid, and a 3'-phosphate linked modified nucleic acid.

15. The support-bound nucleic acid of claim 11, wherein A is phenyl, and Nu is selected from the group consisting of a 5'-phosphate-linked nucleic acid, a 5'-thiophosphate-linked nucleic acid, and a 5'-phosphate linked modified nucleic acid.

16. The support-bound nucleic acid of claim 11, wherein the support material is selected from the group consisting of a silica bead, CPG glass, a polymer bead, a microfluidic cell, and a 96 well plate.

17. The support-bound nucleic acid of claim 16, wherein said polymer bead comprises a polymer selected from the group consisting of polystyrene, agarose, polyacrylate, and polyacrylamide.

18. A method of immobilizing a nucleic acid comprising forming a Schiff-base product by reaction of a compound of Formula:

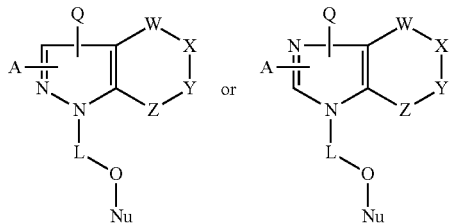

wherein,
W, X, Y, and Z are null, or W, X, Y, and Z comprise a fused benzene ring;
A is selected from the group consisting of aryl, heteroaryl, hydrogen, a $C_1$-$C_4$ alkyl, and halogen;
Q is an aldehyde or protected aldehyde;
L is a linker selected from a $C_1$-$C_{12}$ alkyl, aralkyl, and aryl, any of which is optionally substituted; wherein one or more methylene unit ($CH_2$) of said $C_1$-$C_{12}$ alkyl is optionally replaced by any combination of oxygen, carbonyl($C=O$), and NH; and
Nu is a nucleic acid;
with a support material displaying an amino or masked amino functional group.

19. The method of claim 18, wherein A is hydrogen or methyl, Q is a protected aldehyde, Nu is selected from the group consisting of a 3'-phosphate-linked nucleic acid, a 3'-thiophosphate-linked nucleic acid, and a 3'-phosphate linked modified nucleic acid.

20. The method of claim 18, wherein A is hydrogen or methyl, Q is a protected aldehyde, Nu is selected from the group consisting of a 5'-phosphate-linked nucleic acid, a 5'-thiophosphate-linked nucleic acid, and a 5'-phosphate linked modified nucleic acid.

21. The method of claim 18, wherein A is phenyl, Q is a protected aldehyde, and Nu is selected from the group consisting of a 3'-phosphate-linked nucleic acid, a 3'-thiophosphate-linked nucleic acid, and a 3'-phosphate linked modified nucleic acid.

22. The method of claim 18, wherein A is phenyl, Q is a protected aldehyde, and Nu is selected from the group consisting of a 5'-phosphate-linked nucleic acid, a 5'-thiophosphate-linked nucleic acid, and a 5'-phosphate linked modified nucleic acid.

23. The method of claim 18, wherein the support material is selected from the group consisting of a silica bead, CPG glass, a polymer bead, a microfluidic cell, and a 96 well plate.

24. The method of claim 23, wherein said polymer bead comprises a polymer selected from the group consisting of polystyrene, agarose, polyacrylate, and polyacrylamide.

25. The method of claim 18, wherein the amino or masked amino functional group on the support material is selected from the group consisting of an amine, a hydrazine, an acylhydrazine, a semicarbazide, an aminooxy, a hydrazone, an imine, and an enamine.

26. The method of claim 18, further comprising reduction of the Schiff-base product.

* * * * *